United States Patent [19]

Wienchol et al.

[11] 4,052,165

[45] Oct. 4, 1977

[54] APPARATUS FOR CENTRIFUGAL SEPARATION OF TEST SAMPLES

[75] Inventors: Otto Wienchol, Pullach; Franz Mühlböck, Munich, both of Germany

[73] Assignee: Compur-Electronic Gesellschaft mit beschrankter Haftung, Munich, Germany

[21] Appl. No.: 732,219

[22] Filed: Oct. 14, 1976

[51] Int. Cl.[2] .......................... G01N 33/16; B04B 5/00

[52] U.S. Cl. .......................................... 23/259; 233/26

[58] Field of Search ...................... 23/259, 292; 233/26

[56] References Cited

U.S. PATENT DOCUMENTS

| | | | |
|---|---|---|---|
| 2,507,309 | 5/1970 | Larsson | 233/26 |
| 3,679,367 | 7/1972 | Negersmith et al. | 23/259 |
| 3,720,368 | 3/1973 | Allen | 233/26 |
| 3,748,101 | 7/1973 | Jones et al. | 23/259 |
| 3,891,140 | 6/1975 | Ayres | 233/26 |

*Primary Examiner*—R.E. Serwin

*Attorney, Agent, or Firm*—Stonebraker, Shepard & Stephens

[57] ABSTRACT

A rotor, adapted for rotation at high speeds, has symmetrically arranged radial channels for receiving tubular containers of material to be evaluated, such for example as samples of blood. The outer end of each radially extending container is placed against a resilient abutment at the rim of the rotor, and its inner end is placed against a clamping collar arranged centrally of the rotor and having limited movement in the direction of the axis of rotation. In the initial loading position, the tubular containers are inclined upwardly from the rim toward the center of the rotor. They are clamped firmly into position on the rotor by axial movement of the clamping member which carries the inner ends of the containers downwardly, to force the containers slightly radially outwardly, compressing the resilient abutments at their outer ends. The invention relates to details of construction of the axially movable clamping member, which has a spring tending to move it to unclamping or loading position, and a latch to hold it in clamped position, against the force of the spring.

9 Claims, 6 Drawing Figures

APPARATUS FOR CENTRIFUGAL SEPARATION OF TEST SAMPLES

BACKGROUND OF THE INVENTION

This invention relates to the evaluation or testing of various substances placed in small cylindrical containers, sometimes called cuvets. Such containers are well known in the medical and biological field, and are frequently made of glass tubes of such small diameter that a liquid to be tested is drawn into the tube by capillary action. A typical material frequently tested is blood. The evaluation tests to be made on blood or other substances frequently include the separation of the ingredients or components of the liquid being tested, by subjecting the liquid to centrifugal force, and a subsequent measurement of the separated components.

A basic structure for performing such tests or centrifugal separation procedures comprises a rotor having radial grooves or recesses for receiving the sample containers, with resilient abutments at the outer ends of the containers, and with axially movable clamping means located centrally of the rotor, for receiving the inner ends of the containers. When the clamping means is moved axially to its loading position and the sample containers are placed in the apparatus, the containers are initially inclined upwardly from their outer ends toward their inner ends. Then the clamping member on which the inner ends of the containers rest is moved axially downwardly, to carry the inner ends of the containers downwardly to a straight line position and a little beyond the straight line position; in other words, to carry the inner ends down to the transverse plane (perpendicular to the axis of rotation of the rotor) which contains the outer ends of the containers, and a little beyond such plane, until the containers have a slight downward slope or inclination from their outer ends to their inner ends. Similarly to the action of straightening a toggle, this motion pushes the sample containers slightly radially outwardly into the resilient abutments at their outer ends, thus firmly sealing the outer ends of the respective containers, and at the same time holding them firmly in place for the subsequent high speed rotation of the rotor, to apply the desired centrifugal force to the contents of the containers.

The basic structure for accomplishing this is disclosed in the copending U.S. patent application of Wolfgang König, entitled "Apparatus for centrifugal separation and measurement of samples," Ser. No. 732,218 filed Oct. 14, 1976. The present invention is an improvement on the basic apparatus invented by König, the improvement relating to various details of the construction of the clamping means, including the provision of a spring tending to move a clamping member axially from clamped position to unclamped or loading position, and a latch for holding the clamping member in its clamping position until the latch is released.

An object of the present invention is to improve the basic König structure by providing a better and more easily operated clamping means, more easily and quickly operable by the user, and having greater certainty of remaining in clamped position during high speed rotation of the parts, eliminating any possibility of accidental movement from clamped position to unclamped or loading position.

This object is well fulfilled by apparatus according to the construction herein disclosed as an example of a preferred embodiment of the invention.

DESCRIPTION OF THE PREFERRED EMBODIMENT

As above stated, the present invention is in the nature of an improvement on the basic structure disclosed in the above mentioned application of Wolfgang König, and relates particularly to the clamping means disclosed broadly in that application. The entire disclosure of the König application in incorporated herein by reference.

Figure 3:
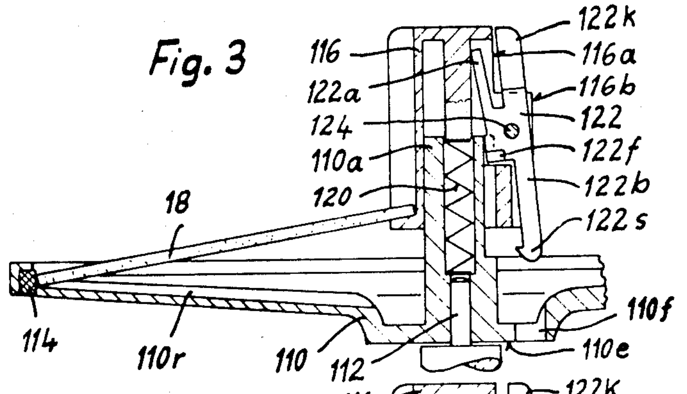
FIG. 3 is a view similar to FIG. 1, with the clamping means in unclamped or loading and unloading position.
Figure 1:
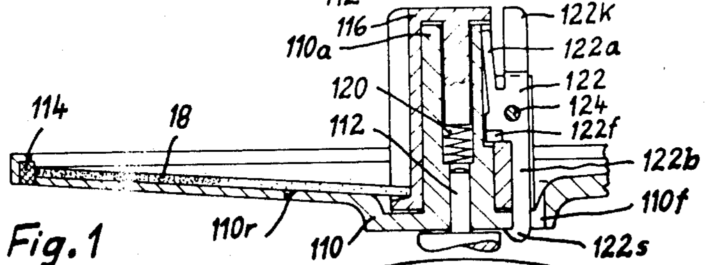
FIG. 1 is diametrical section through the rotor and the improved clamping means of the present invention, showing the clamping means in clamping position.

The apparatus includes a rotor 110 in the form of a circular plate of slightly dished shape as seen in diametrical axial section in FIGS. 1 and 3. The hub portion **110*a* of the rotor is firmly mounted on a shaft 112** having a suitable drive of known form for rotating the shaft at high speed. It may be, for example, the shaft of a conventional centrifuge.

On the upper surface of the rotor plate are any desired number of symmetrically arranged radially extending grooves **110*r* for receiving tubular containers or cuvets 18 containing the blood or other material to be evaluated or tested. Four such grooves or radial recesses are here illustrated, but more or less may be used. The outer rim of the rotor has an upstanding marginal flange with appropriate openings for insertion, opposite the other end of each recess or groove, of a resilient buffer or abutment 114** of resilient compressible material with good sealing properties, such as natural or artificial rubber.

The hub portion **110*a* extending upwardly from the main body of the rotor is surrounded by clamping means in the form of a clamping collar or sleeve 116 fitting snugly but axially slidably on the hub. A coiled compression spring 120 seated in an axial bore in the hub member 110*a* presses downwardly on a shoulder in this axial bore and presses upwardly on a central pin portion of the clamping collar or sleeve 116**, constantly tending to move this collar upwardly on the rotor hub.

Figure 4:
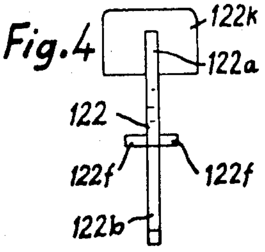
FIG. 4 is a side elevational view of a latching lever according to the invention, removed from the rest of the mechanism.

A latch member 122, pivotally mounted on the clamping collar 116 by means of a pivot 124, has a lower end which projects down through an opening **110*f* in the rotor when the clamping collar is in its lowermost position, as seen in FIG. 4, and this lower end has a lateral projection or hook-like portion 122*s* which, in the latched position, engages a bottom abutment surface 110*e* of the rotor and holds the clamping collar 116 in its lower position, against the upward force of the spring 120, until the latch is released. The clamping member 116 is flattened at 116*a* and is partially slotted radially and axially at 116*b*, the flat arm 122*b* of the latch member 122 being accommodated in this slot. The upper end of the latch lever, above the pivot 124 thereof, is provided with a wide head 122*k* which is opposite the flattened portion 116*a*, and which provides a convenient operating portion for contact with a thumb or finger of the user, to be swung radially inwardly toward the axis of rotation in order to swing the lower end 122s outwardly to release the latch and permit the clamping member to move upwardly under the influence of its spring 120.**

The latch lever 122 has a further arm 122a which slips into a vertical guide slot 110s in the hub 110 (FIGS. 5 and 6) during the axial movement of the clamping member 116. This, together with the position of the arm 122b in the opening 110f of the hub, serves to couple the clamping member 116 to the hub 110 in a rotational sense, to insure that the clamping member rotates bodily with the rotor.

Figure 5:
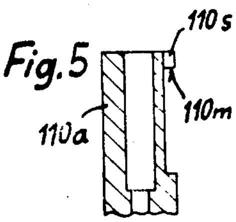
FIG. 5 is an axial diametrical section through a portion of the rotor hub, illustrating details.
Figure 6:
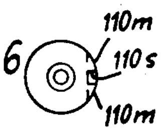
FIG. 6 is a top plan view of the hub shown in FIG. 5.

The hub 110a is flattened below the guide slot 110s so that there are two projections or noses 110m on either side of the vertical slot 110s, as illustrated in FIGS. 5 and 6. These noses cooperate with lateral lugs 122f on the latching lever 122, and serve to limit the upward extent of axial movement of the clamping member under the influence of its spring 120. The engagement of the parts 122f and 110m thus define the upper limit position or unclamped loading position of the clamping means.

Figure 2:
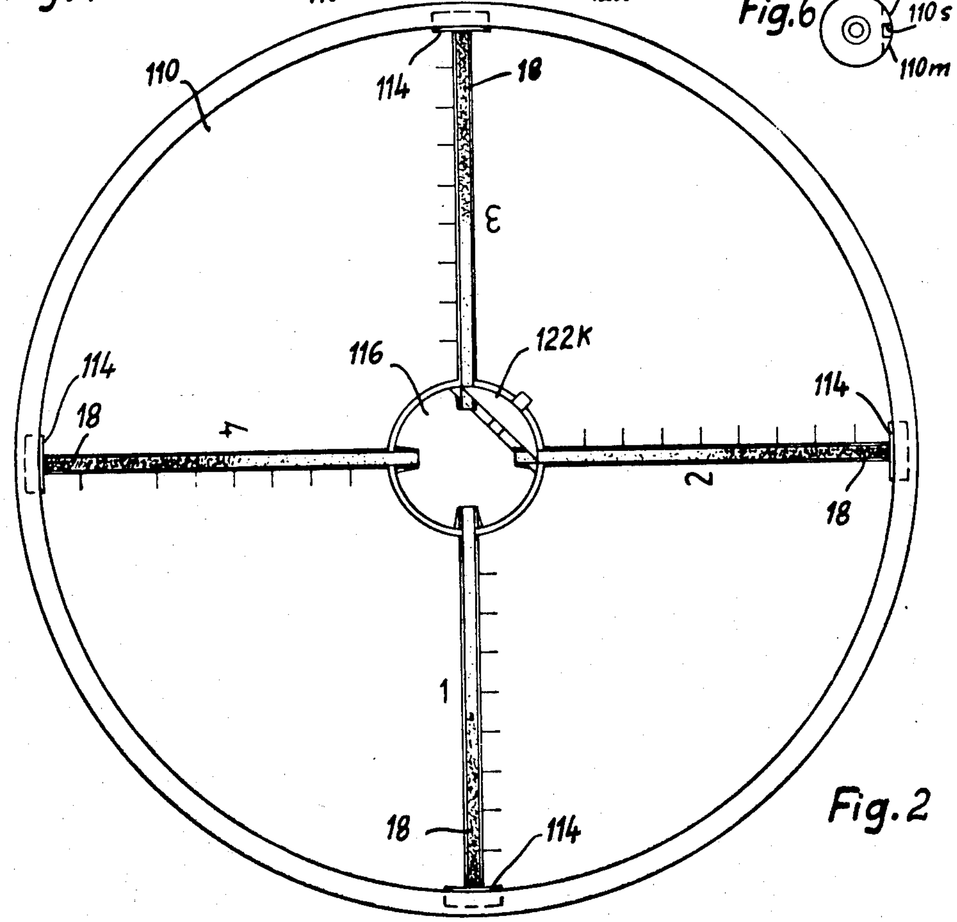
FIG. 2 is a plan of the parts shown in FIG. 1.

The sample containers or cuvets are intially loaded in the apparatus in the position illustrated in FIG. 3, with the outer end of each container 18 resting against the resilient abutment 114, and the inner end resting on a ledge at the bottom of a vertical groove in the clamping collar 116, as illustrated in FIG. 2 and 3. Thereupon, the clamping collar 116 is moved downwardly by hand, against the force of the spring 120, until the nose 122s on the latching lever 122 latches against the abutment surface 110e on the rotor, this position being illustrated in FIG. 1. During the downward movement, the sample container 18 is moved slightly radially outwardly because of the toggle effect, compressing the abutment 114, to what may be called a straight line or dead center position, and then slightly downwardly a little further beyond the dead center position, until each cuvet 18 is seated in its individual radial recess or groove 110r, with the outer end of the container still tightly engaged with and somewhat compressing the resilient abutment 114, to seal the outer end tightly. In this final clamping position, the container 18 is inclined relative to the transverse plane containing the outer end of the cuvet, in a downward direction from the outer end to the inner end, but at somewhat less inclination or angle to the transverse plane than the angle of previous upward inclination in the loading position (FIG. 3).

Any possible danger of premature upward movement of the clamping member is prevented by the positive latch provided by the cooperating parts 122s and 110e. The tight clamping of the sample containers 18 cannot be released until the operating surface 122k is moved radially inwardly toward the axis of rotation, in order to release the latch.

Advantageously the arm 122a on the latch is slightly resilient, and its engagement with the hub 110a causes a force tending to turn the latch 122 in a clockwise direction (viewed as in FIGS. 1 and 3) on the pivot 124, thus resiliently keeping the latch in its latching position when the clamping collar 116 is in its lower or clamping position. In the upper or unclamping position shown in FIG. 3, the arm 122a is no longer in contact with a portion of the hub 110a but is above the top end of this hub, as illustrated, thereby releasing the resilient clockwise force on the latching lever in this upper position, but providing such resilient clockwise force in the lower position of the parts (FIG. 1) as the arm 122a of the latching lever comes down to a position opposite and is engaged by the upper portion of the hub 110a.

The parts 110, 116, and 122 are advantageously made as injection moldings, which enables favorable and economic mass production of the clamping assembly. With the arrangement according to the present invention, the cuvets or sample containers can always be inserted and gripped in a definite predetermined position of the parts, with the clamping member 116 in a definite loading position under the influence of the spring 120, and then can be fully and tightly clamped when the clamping member is moved downwardly to its clamping position, without danger of accidental release during the high speed rotation of the parts.

The radial recesses 110r for receiving the tubular containers are preferably individually numbered, as by the numerals "1", "2", "3", and "4" shown in FIG. 2. Graduated scales are preferably marked alongside each recess, as also seen in FIG. 2, to enable a numerical reading of the proportion of heavy components to light components in each tubular vessel at the conclusion of the centrifuging operation.

What is claimed is:

1. Apparatus for centrifugal separation of test samples in containers of tubular form open at both ends, said apparatus comprising a rotor of plate-like form having a plurality of radially extending recesses each being adapted to accommodate one of said tubular containers, resilient abutment means on said rotor at the outer end of each recess in position to serve as an abutment for the outer end of a tubular container laid in such recess, clamping means mounted centrally on said rotor and movable axially from a loading position to a clamping position, said clamping means forming a movable abutment for the inner ends of the tubular containers, said axial movement of said clamping means carrying the inner ends of the tubular containers from a position on one side of a transverse plane perpendicular to the axis of rotation of said rotor and containing the outer ends of said containers to a position on the opposite side of said plane, and said axial movement of said clamping means serving to displace a tubular container radially outwardly into tight sealing and clamping engagement with said resilient abutment means, characterized by the provision of a spring tending to maintain said clamping means in its loading position, and a latch for holding said clamping means in its clamping position against the force of said spring.

2. Apparatus as defined in claim 1, wherein said rotor includes a central axially extending guide portion and said clamping means includes a collar member movable axially along said guide portion, said collar member having a portion for receiving and abutting against the inner end of a tubular container when the outer end of such container is placed in one of said radial recesses in engagement with said resilient abutment means, said spring tending to maintain said collar member in a loading position wherein said tubular container is inclined at a substantial angle to a plane perpendicular to the axis of rotation of said rotor, said latch holding said collar member in a clamping position wherein said tubular container is inclined at a lesser angle to said plane and is tightly compressed longitudinally of said container between said resilient abutment means at its outer end and a portion of said collar member at its inner end.

3. Apparatus as defined in claim 2, wherein the inclination of said tubular member when in clamped position is in an opposite direction relative to said plane from the direction of inclination when it is in an unclamped loading position.

4. Apparatus as defined in claim 1, wherein said rotor includes means forming an axially extending guide groove, and said clamping means includes a part engaged in said guide groove to couple said clamping means to said rotor to rotate bodily therewith.

5. Apparatus as defined in claim 4, wherein said latch is pivotally mounted on said clamping means, and said part engaged in said guide groove is a part of said latch.

6. Apparatus as defined in claim 1, further comprising cooperating abutment surfaces on said rotor and said clamping means for determining the loading position to which said clamping means is moved by said spring.

7. Apparatus as defined in claim 6, wherein said clamping means includes an axially movable collar member, said latch is pivotally mounted on said collar member, and one of said cooperating abutment surfaces is a surface on said latch.

8. Apparatus as defined in claim 7, wherein said latch has one arm with a detent portion cooperating with a part of said rotor to hold said clamping means in its clamping position, and said latch also has another arm having an operating surface for manual engagement to release the latch.

9. Apparatus as defined in claim 1, wherein said latch has one arm with a detent portion cooperating with a part of said rotor to hold said clamping means in its clamping position, and said latch also has another arm having an operating surface for manual engagement to release the latch.

* * * * *

UNITED STATES PATENT AND TRADEMARK OFFICE

CERTIFICATE OF CORRECTION

PATENT NO. : 4,052,165

DATED : October 4, 1977

INVENTOR(S) : Otto Wienchol and Franz Mühlböck

It is certified that error appears in the above-identified patent and that said Letters Patent are hereby corrected as shown below:

On the cover sheet, add:

--[30] Foreign Application Priority Data

July 6, 1976 Germany 2630360.--

Signed and Sealed this

*Twenty-seventh* Day of *December 1977*

[SEAL]

*Attest:*

RUTH C. MASON
*Attesting Officer*

LUTRELLE F. PARKER
*Acting Commissioner of Patents and Trademarks*